(12) United States Patent  
Joshi

(10) Patent No.: US 7,172,734 B1
(45) Date of Patent: Feb. 6, 2007

(54) SANITIZING DEVICE AND ASSOCIATED METHOD

(76) Inventor: Ashok V. Joshi, 4552 S. Thousand Oaks Dr., Salt Lake City, UT (US) 84124

( * ) Notice: Subject to any disclaimer, the term of this patent is extended or adjusted under 35 U.S.C. 154(b) by 0 days.

(21) Appl. No.: 09/603,179

(22) Filed: Jun. 26, 2000

(51) Int. Cl.
*H01M 6/18* (2006.01)

(52) U.S. Cl. .............. 422/186; 204/194; 422/186.05; 429/33; 429/304

(58) Field of Classification Search ............ 422/1, 422/28, 37, 121, 122, 123, 124, 186.04, 22, 422/186, 905, 40; 210/764, 198, 259, 232; 204/620, 618, 621, 335, 345, 349
See application file for complete search history.

(56) References Cited

U.S. PATENT DOCUMENTS

| | | | | |
|---|---|---|---|---|
| 4,020,246 A | * | 4/1977 | Seo et al. .................. 429/104 |
| 4,048,030 A | * | 9/1977 | Miller ...................... 205/701 |
| 4,161,435 A | * | 7/1979 | Moeglich .................. 204/149 |
| 4,265,727 A | * | 5/1981 | Beckley .................... 204/242 |
| 4,474,620 A | * | 10/1984 | Hall ........................ 210/257.1 |
| 4,485,519 A | * | 12/1984 | Collier ....................... 15/359 |
| 4,548,716 A | * | 10/1985 | Boeve ....................... 210/652 |
| 4,583,548 A | * | 4/1986 | Schmid ..................... 600/396 |
| 4,617,157 A | * | 10/1986 | Stein et al. ................. 422/124 |
| 5,207,877 A | * | 5/1993 | Weinberg et al. ........... 204/149 |
| 5,364,512 A | * | 11/1994 | Earl ........................ 210/138 |
| 5,427,667 A | * | 6/1995 | Bakhir et al. .............. 204/260 |
| 5,460,705 A | * | 10/1995 | Murphy et al. ............. 204/252 |
| 5,493,754 A | * | 2/1996 | Gurstein et al. ............. 15/321 |
| 5,635,039 A | * | 6/1997 | Cisar et al. ................ 204/252 |
| 5,766,789 A | * | 6/1998 | James et al. ................. 429/44 |
| 5,770,033 A | * | 6/1998 | Murphy et al. ............. 205/264 |
| 5,779,912 A | * | 7/1998 | Gonzalez-Martin et al. ....................... 422/186.3 |
| 5,824,274 A | * | 10/1998 | Long .......................... 708/140 |
| 5,972,196 A | * | 10/1999 | Murphy et al. ............. 205/466 |
| 6,007,943 A | * | 12/1999 | Coetzer ..................... 429/104 |
| 6,120,822 A | * | 9/2000 | Denvir et al. .............. 426/320 |
| 6,134,806 A | * | 10/2000 | Dhaemers .................... 34/404 |
| 6,296,744 B1 | * | 10/2001 | Djeiranishvili et al. ..... 204/263 |
| 6,387,241 B1 | * | 5/2002 | Murphy et al. ............. 205/626 |
| 6,391,183 B1 | * | 5/2002 | Tanioka et al. ............. 205/626 |
| 6,458,257 B1 | * | 10/2002 | Andrews et al. ............ 204/263 |
| 2003/0080467 A1 | * | 5/2003 | Andrews et al. ............ 264/275 |

* cited by examiner

*Primary Examiner*—Krisanne Jastrzab
(74) *Attorney, Agent, or Firm*—David Fonda

(57) ABSTRACT

A sanitizing device comprising: a sanitizing component for sanitizing a surface, liquid, gas, and/or associated surrounding environment, wherein the sanitizing component includes an electrochemical, chemical, and/or corona cell; and a housing for retaining the sanitizing component. A particulate filtering component capable of substantially trapping particulates thereon and fragrance emitting means are also provided.

3 Claims, 4 Drawing Sheets

SANITIZING DEVICE AND ASSOCIATED METHOD

BACKGROUND OF THE INVENTION

1. Field of the Invention

The present invention relates in general to a sanitizing device having an electrochemical, chemical, and/or corona cell, and more particularly, to a sanitizing device having an electrochemical, chemical, and/or corona cell as a component to sanitize, disinfect, sanitize, and/or otherwise beneficially effect surfaces, liquids, gasses, and/or associated surrounding environments.

2. Background Art

Sanitizing devices have been known in the art for several years and are the subject of many United States patents including: U.S. Pat. No. 5,874,050; U.S. Pat. No. 5,441,710; U.S. Pat. No. 3,691,346; U.S. Pat. No. 3,654,432; and U.S. Pat. No. 5,928,481.

U.S. Pat. No. 5,874,050 discloses a room air sterilization device having an elongated member with a plurality of narrow, substantially parallel passages extending from a first end to a second end. Heating wire, preferably fabricated from a nickel chromium resistive material, is positioned within the passages. Upon application of a power source, including AC/DC current, the heating wire radiates heat within the passages, thereby raising the air to a sufficient temperature to become sterilized and rise from the passage via convection current.

U.S. Pat. No. 5,441,710 discloses an air flow sterilizer for destroying microorganisms by heating an air flow to a sufficient temperature to weaken cellular walls of the microorganisms. Turbulence is introduced into the air flow so that the weakened microorganisms are destroyed upon hitting a surface of the turbulent chamber.

U.S. Pat. No. 3,654,432 discloses an electrically heated catalytic air purifier having a heating unit for treating air borne particles. The heating unit includes a surface coating of silicon carbide which functions at an operating temperature between 250 and 350 degrees centigrade.

U.S. Pat. No. 5,928,481 discloses an apparatus for sterilizing water by the process of heavy metal sterilization using silver.

SUMMARY OF THE INVENTION

The present invention is directed to a sanitizing device comprising: (a) a sanitizing component for sanitizing a surface, liquid, gas, and/or associated surrounding environment, wherein the sanitizing component includes an electrochemical, chemical, and/or corona cell; and (b) a housing for retaining the sanitizing component.

In a preferred embodiment of the invention, the sanitizing component comprises a porous matrix substantially impregnated with a material selected from the group consisting essentially of peroxides, superoxides, fluorates, chlorates, bromates, iodates, permanganates, and mixtures thereof. In this embodiment the porous matrix may comprise one or more materials selected from the group consisting essentially of plastics, carbonaceous materials, ceramics, metals, and mixtures thereof.

In another preferred embodiment of the invention the sanitizing device further comprises power means for powering an electrochemical and/or corona cell, wherein the power means consists of AC current and/or DC current. In this embodiment the sanitizing component preferably comprises the electrochemical and/or corona cell.

If a corona cell is associated with the sanitizing device of the present invention, it is preferred that such a corona cell comprise a dielectric material and two electrodes.

If an electrochemical cell is associated with the sanitizing device of the present invention, it is preferred that such an electrochemical cell include an anodic component, a cathodic component, and an electrolyte component. The electrolyte component may comprise a solid phase material, and may also serve as a partial or full component of the device, such as, for example, a housing, porous matrix, or particulate filtering component.

Preferably both the anodic component and the cathodic component comprise the same or different materials selected from the group consisting essentially of metals such as, titanium, nickel, steel, copper, silver, platinum, palladium, zinc, aluminum, and mixtures and alloys thereof, and conductive ceramics such as, perovskites, carbides and nitrides of metals.

In yet another preferred embodiment of the invention, the electrolyte component comprises a material selected from the group consisting essentially of a halide containing material, an oxide containing material, an ion exchange membrane, an alkali ion conducting material, a silver or copper ion conducting material, and an ion conducting ceramic material and mixtures, compounds, and alloys thereof. In this embodiment the halide containing material may include halides of metals, their mixtures and compounds as well as their composites with plastic and ceramic materials. Oxide containing materials may include composites of metal oxides and ion conducting materials (e.g. $AgI$—$Al_2O_3$ composites) as well as beta-aluminas's ($M_xO$-$11Al_2O_3$) or Nasicon materials.

In accordance with the present invention, an ion exchange membrane may comprise Nafion, Nasicon, and/or beta-alumina materials in which any monovalent or divalent ion can be substituted such as, for example, Ag, Cu, Li, Rb, Cs, Na, H, Mg, Etc.

In accordance with the present invention, silver and copper ion conducting materials may include inorganic and/or organic compounds of silver and/or copper (e.g. halides, chalcogenides, phosphates, tungstates, zirconates, aluminates, and titanates of silver and/or copper), which have ionic conductivity greater than approximately $10^{-10}$ $(ohm\ cm)^{-1}$ at ambient temperatures.

In accordance with the present invention alkali ion conducting materials may include lithium, sodium, rubidium, cesium ion conducting materials with ionic conductivity greater than approximately $10^{-10}$ $(ohm\ cm)^{-1}$ at ambient temperatures.

In yet another preferred embodiment of the present invention, the dielectric material of an associated corona cell may comprise a material selected from the group consisting of an oxide containing ceramic material and/or plastic material having a dielectric constant less than 100 and an electronic conductivity less than $10^{-7}$ $(ohm\ cm)^{-1}$.

In accordance with the present invention, an electrode associated with a corona cell may comprise materials selected from the group consisting essentially of metals such as, for example, titanium, nickel, steel, copper, silver, platinum, tungsten, palladium, aluminum, and mixtures and alloys thereof, as well as conductive ceramics such as, perovskites, carbides and nitrides of metals and mixtures thereof.

In a preferred embodiment of the invention, a particulate filtering component may also be associated with the housing which is capable of substantially trapping particulates thereon, such as an activated carbonaceous filter component.

Preferably the sanitizing device of the present invention is also associated with forced air means including a fan, a blower, etc.

The present invention is also directed to a multi-layer composite sanitizing device comprising: (a) a sanitizing component associated with a housing for sanitizing a surface, liquid, gas, and/or associated surrounding environment, wherein the sanitizing component includes an electrochemical, chemical, and/or corona cell; (b) a particulate filtering component capable of substantially trapping particulates thereon; and (c) a housing for retaining the sanitizing component and the particulate filtering component.

The present invention is further directed to a process for sanitizing a surface comprising the steps of: (a) providing a sanitizing component such as an electrochemical, chemical, and/or corona cell retained within a housing; (b) contacting the sanitizing component of the device with a surface; and (c) substantially sanitizing the surface.

The present invention is further directed to a process for sanitizing a liquid, gas and/or other matter, comprising the steps of: (a) providing a sanitizing component such as an electrochemical, chemical, and/or corona cell retained within a housing; (b) passing liquid, gas, and/or other matter over the sanitizing component; (c) contacting sanitizing component with the liquid, gas, and/or other matter; and (d) substantially sanitizing the liquid, gas, and/or other matter.

BRIEF DESCRIPTION OF THE DRAWINGS

The invention will now be described with reference to the drawings wherein.

DETAILED DESCRIPTION OF THE INVENTION

Figure 1:
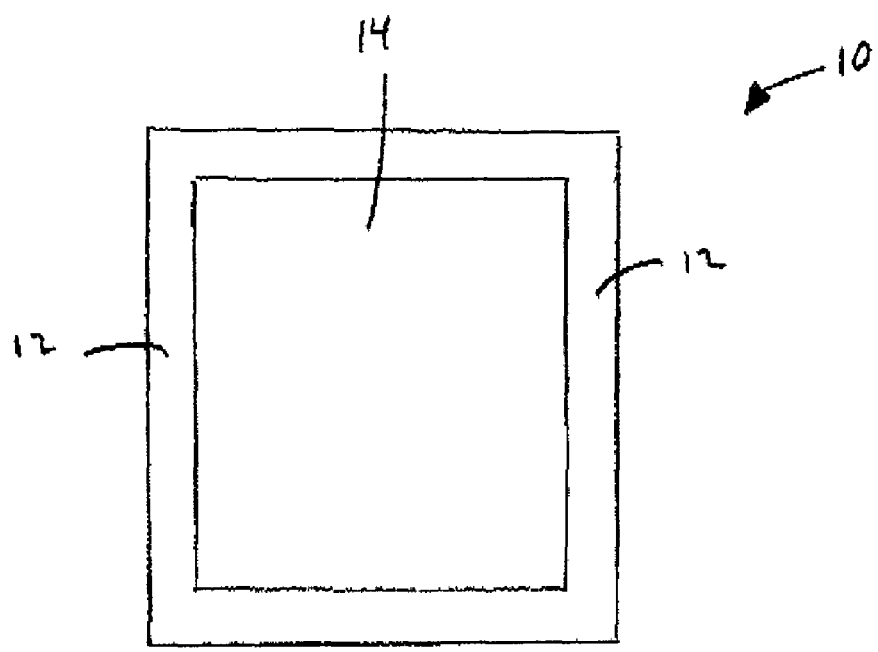
FIG. 1 of the drawings is a schematic representation of a sanitizing device in accordance with the present invention.

While this invention is susceptible of embodiment in many different forms, there is shown in the drawings and described herein in detail several specific embodiments with the understanding that the present disclosure is to be considered as an exemplification of the principles of the invention and is not intended to limit the invention to the embodiments illustrated.

It will be understood that like or analogous elements and/or components, referred to herein, are identified throughout the drawings by like reference characters. In addition, although the term "sanitizing" will be used throughout the disclosure, it should be understood that the device is also capable of "purifying" as well.

Referring now to the drawings and to FIG. 1 in particular, sanitizing device 10 is shown in a first embodiment as generally comprising housing 12 and sanitizing component 14 for sanitizing contaminants, such as microorganisms, germs, bacteria, viruses, undesirable chemicals and/or compounds, etc. Housing 12 may be fabricated from any one of a number of materials including natural and synthetic resins, plastics, metals, woods, etc. While sanitizing device 10 has been shown as being substantially rectangular, numerous other geometric configurations are likewise contemplated for use including generally circular, generally elliptical, generally square, generally triangular, generally polygonal, and generally arbitrary—just to name a few.

For purposes of the present invention, sanitizing component 14 includes an electrochemical, chemical, and/or corona cell or purifier. The chemical purifier preferably comprises a porous matrix substantially impregnated with one or more of the following materials, namely: peroxides; superoxides; fluorates; chlorates; bromates; iodates; and permanganates. While it is desirous for the above-identified materials to be relatively pure, the presence of nominal amounts of other materials does not appear to be detrimental to the present invention—so long as the concentration of the sanitizing material remains high enough to perform its intended function of killing a substantial majority of the above-identified contaminants. The porous matrix of sanitizing component 14 is preferably fabricated from carbonaceous materials, plastics, ceramics, metals, and mixtures thereof.

Figure 2:
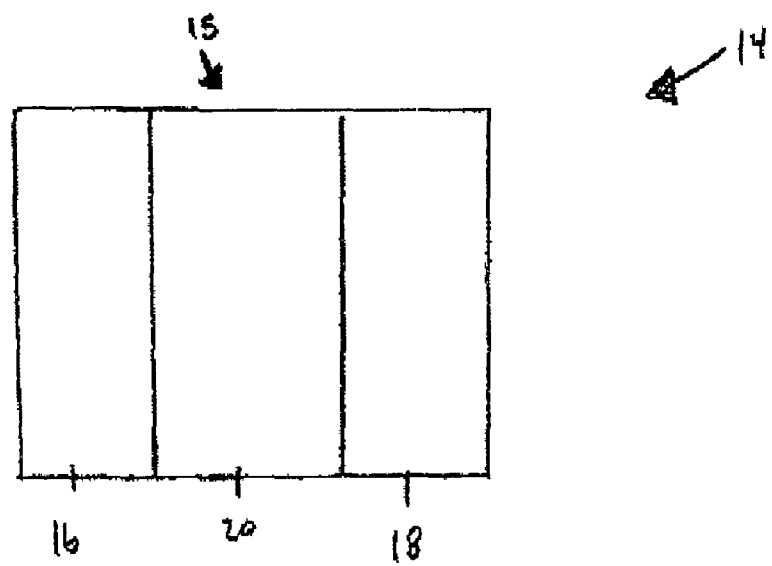
FIG. 2 of the drawings is a fragmented side view of a sanitizing device in accordance with the present invention showing an electrochemical sanitizing component.

When an electrochemical and/or corona cell or purifier is incorporated into sanitizing device 10, it may be operated by AC current and/or DC current. However, numerous other power means that would be known to those having ordinary skill in the art are likewise contemplated for use. As is shown in FIG. 2, sanitizing component 14 may include an electrochemical cell 15 comprising anodic component 16, cathodic component 18, and electrolyte component 20.

Anodic component 16 and cathodic component 18 may be fabricated from the same or different materials, including metals, conductive ceramics (including a particulate filtering component), and mixtures thereof. Preferred metals include transitions metals such as titanium, nickel, copper, silver, platinum, palladium, zinc, as well as aluminum, steel, and mixtures and alloys thereof, and preferred conductive ceramics include perovskites, carbides, nitrides of metals, and mixtures thereof.

While preferred anodic and cathodic component materials have been disclosed, for illustrative purposes only, it will be understood that numerous other conventional anodic and cathodic materials are likewise contemplated for use.

Electrolyte component 20 may be fabricated from several materials including, for example, a halide containing material, an oxide containing material, an ion exchange membrane, an alkali ion conducting material, a silver or copper ion conducting material, and an ion conducting ceramic material and mixtures, compounds, and alloys thereof.

Preferred halide containing materials include halides of metals, their mixtures and compounds as well as their composites with plastic and ceramic materials. For example, the halide containing material may include one or more of the following materials, $PbI_2$, $PbF_2$, $LaF_3$, $AgRbI_5$, $AgI$—$Al_2O_3$, $CuI$—$Al_2O_3$, and mixtures thereof In accordance with the present invention, oxide containing materials may include composites of metal oxides and ion conducting materials (e.g. $AgI$—$Al_2O_3$ composites) as well as beta-aluminas's ($M_xO$-$11Al_2O_3$) or Nasicon materials.

Preferably, an ion exchange membrane may comprise Nafion, Nasicon, and/or beta-alumina materials in which any monovalent or divalent ion can be substituted such as, for example, Ag, Cu, Li, Rb, Cs, Na, H, Mg, Etc.

Suitable silver and copper ion conducting materials may include inorganic and/or organic compounds of silver and/or copper (e.g. halides, chalcogenides, phosphates, tungstates, zirconates, aluminates, and titanates of silver and/or copper), which have ionic conductivity greater than approximately $10^{-10}$ (ohm cm)$^{-1}$ at ambient temperatures.

In accordance with the present invention, alkali ion conducting materials may include lithium, sodium, rubidium, cesium ion conducting materials with ionic conductivity greater than approximately $10^{-10}$ (ohm cm)$^{-1}$ at ambient temperatures.

While several specific electrolyte components have been disclosed, for illustrative purposes only, it will be understood that other electrolyte components are suitable for use in accordance with the present invention—so long as the particular material(s) substantially sanitize associated contaminants contained therein.

If a corona cell is associated with the present invention, such cell may comprise electrode materials selected from the group consisting essentially of metals such as, for example, titanium, nickel, steel, copper, silver, platinum, tungsten, palladium, aluminum, and mixtures and alloys thereof, as well as conductive ceramics such as, perovskites, carbides and nitrides of metals and mixtures thereof. Further, if a corona cell is associated with the present invention, then such a cell may comprise dielectric materials selected from the group consisting of metal oxides such as titanium, aluminum and silicon oxides.

Figure 3:
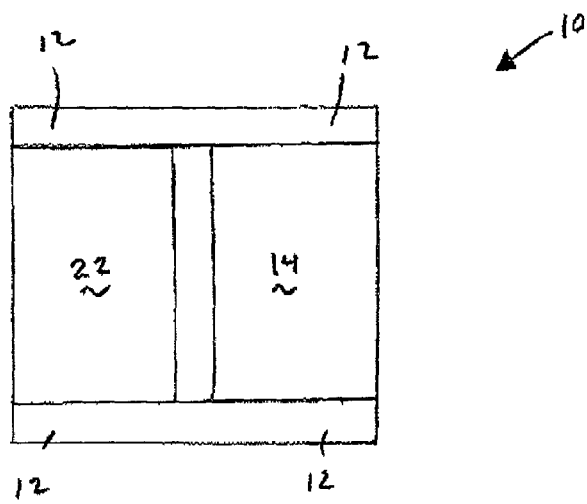
FIG. 3 of the drawings is a side view of a sanitizing device accordance with the present invention showing an electrochemical sanitizing component associated with a particulate filtering component.

As is shown in FIG. 3, particulate filtering component 22 may also be associated with the sanitizing device 10. Particulate filtering component 22 is capable of substantially trapping particulates thereon, and is preferably fabricated from activated carbonaceous material(s). Particulate filtering component 22 is also capable of deodorizing an associated unclean medium (e.g. liquids including water, gasses including air, and mixtures of both). In accordance with the present invention, particulate filtering component 22 traps relatively larger components of an unclean medium, such as air borne dust, hair, dirt, etc. In this embodiment particulate filtering component 22 may be positioned in front or behind sanitizing component 14, although it is preferred that sanitizing component 14 is positioned behind particulate filter component 22 so that incoming medium will contact the particulate filtering component first.

Figure 4:
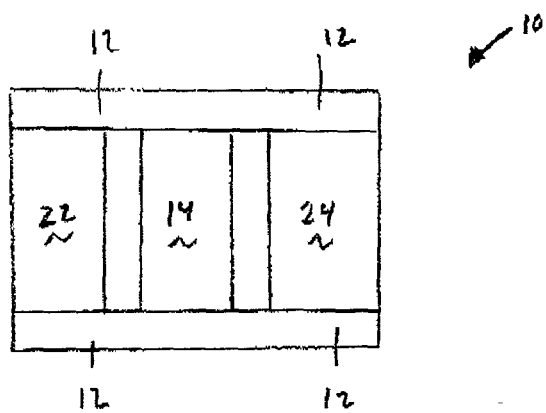
FIG. 4 of the drawings is a side view of a sanitizing device in accordance with the present invention showing an electrochemical sanitizing component associated with both a particulate filtering component as well as with fragrance emitting means.

As is shown in FIG. 4, sanitizing device 10 may also include fragrance emitting means 24, such as a conventional electrochemical fragrance dispenser or a porous matrix material (as disclosed above) impregnated with a id fragrant material. In this embodiment, the precise order of each component is not critical, however, it is preferred that particulate filtering component 22 is positioned before sanitizing component 14, and that fragrance emitting mean is positioned last so that incoming medium will be filtered for particulates and disinfected prior to being associate with a fragrant material.

Figure 5:
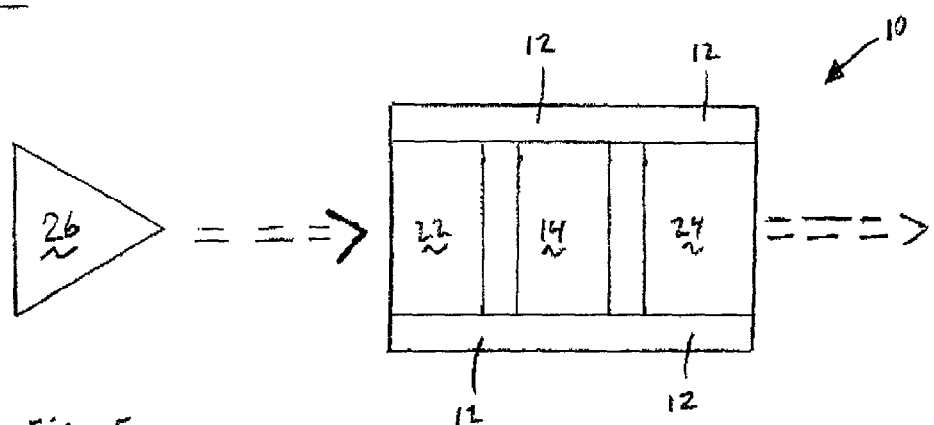
FIG. 5 of the drawings is a side view of a sanitizing device in accordance with the present invention associated with forced air means.

As is shown schematically in FIG. 5, sanitizing device 10 may also be associated with forced air means 26, such as a fan, a blower, etc. In this embodiment, unclean medium (in this case air) is directed to the device so that the sanitizing process can be expedited.

While specific multi-layer composite device configurations have been disclosed, for illustrative purposes only, it will be understood that numerous multi-layer composite configurations are contemplated for use including, but by no means limited to, the following: AB; BA; BC; CB; ABC; BCA; CBA; AAB; BBC; ABAC, ABBC, AABBCC; and ABCABC:

Wherein A=a particulate filtering component;
Wherein B=a sanitizing component; and
Wherein C=fragrance emitting means.

In operation, when a sanitizing component retained within a housing is only provided, unclean medium passes through sanitizing device 10, whereby the unclean medium having contaminants contacts sanitizing component 14. Upon contact with the sanitizing component, the contaminants contained within the unclean medium are beneficially altered or killed by "active materials" either impregnated into the porous matrix (in the case of a chemical purifier) or contained within an electrode or the electrolyte (in the case of an electrochemical purifier).

Alternatively, if particulate filtering component 22 is also associated with sanitizing device 10, the unclean medium preferably first passes through particulate filtering component 22, whereupon particulates are substantially trapped and do not continue into the sanitizing component. Adding such a component is desirous for conditions where relatively larger particulates may be found such as dirt, dust, hair, etc.

In addition, when fragrance emitting means 24 are associated with sanitizing device 10, the unclean medium is preferably impregnated with a desirable fragrance just prior to exiting the filter. As such, although not necessary, it is preferable to have fragrance emitting means positioned as the last sanitizing device component.

It will be understood that sanitizing device 10 may be incorporated into any one of a number of sanitizing applications. For example, sanitizing device 10 may be configured for use in association with AC and/or DC powered portable air sanitizing devices. Alternatively, sanitizing device 10 may be configured to replace or supplement conventional filters in forced air heating/cooling systems including those in homes, commercial building, vehicles, airplanes, boats, etc. In such an application, sanitizing device 10 may be positioned in several places including, immediately prior or subsequent to any forced air means, immediately prior to a vent or register—just to name a few.

Figure 6:
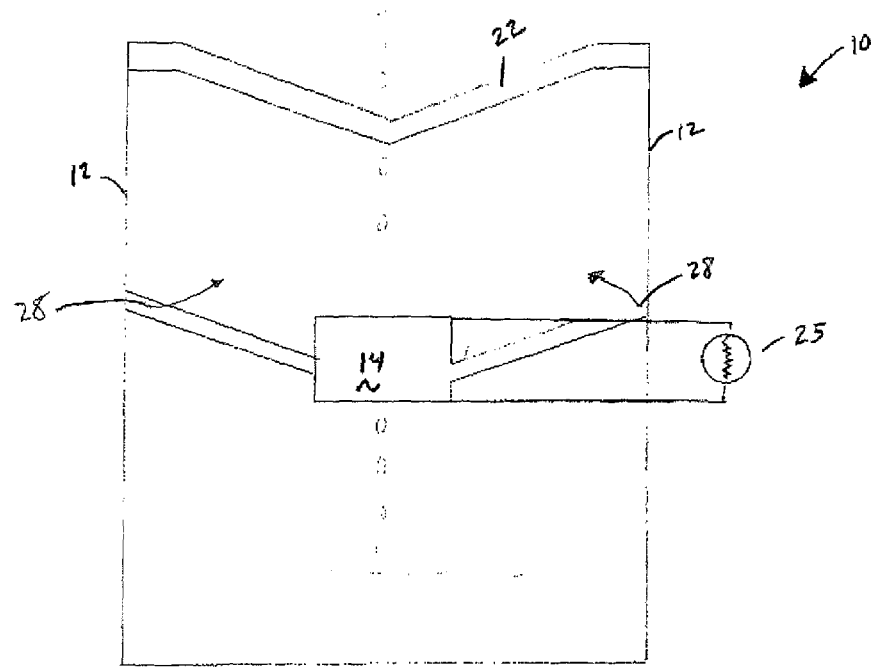
FIG. 6 of the drawings is a schematic representation of a sanitizing device in accordance with the present invention configured as a water purifier.

As is shown in FIG. 6, sanitizing device 10 may be operatively configured as a portable water purifier. In this embodiment sanitizing device 10 generally comprises housing 12, sanitizing component 14, filtering component 22, and reservoir member 28. For purposes of the present disclosure sanitizing component 14 may comprise an electrochemical and/or corona cell which is powered by AC current and/or DC current 25. Preferably the sanitizing component includes an electrochemical and/or corona cell that is generally porous so that water or other media can transport through such a cell.

In operation, a user pours a medium, such as water, on the top of filtering component 22, whereby particulates are isolated on top of the filtering component. Next the medium is gravity fed into reservoir member 28, whereupon the medium contacts sanitizing component 14. In accordance with above-identified embodiments, sanitizing member 14 purifies the medium upon contact. Once purified the medium is retained within the bottom of housing 12 for subsequent use.

Figure 7:
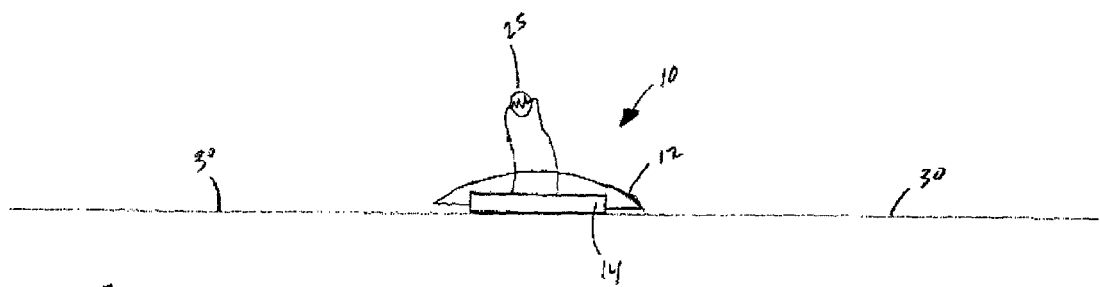
FIG. 7 of the drawings is a schematic representation of a sanitizing device in accordance with the present invention configured as a surface disinfectant device.

As is shown in FIG. 7, sanitizing device 10 may be operatively configured as a surface disinfectant device. In this embodiment sanitizing device 10 generally comprises housing 12 and sanitizing component 14. For purposes of the present disclosure sanitizing component 14 may comprise an electrochemical and/or corona cell which is powered by AC current and/or DC current 25. In operation, a user places sanitizing device 10 onto surface 30, whereupon application of an applied potential to sanitizing component 14, surface 30 is purified.

Figure 8:
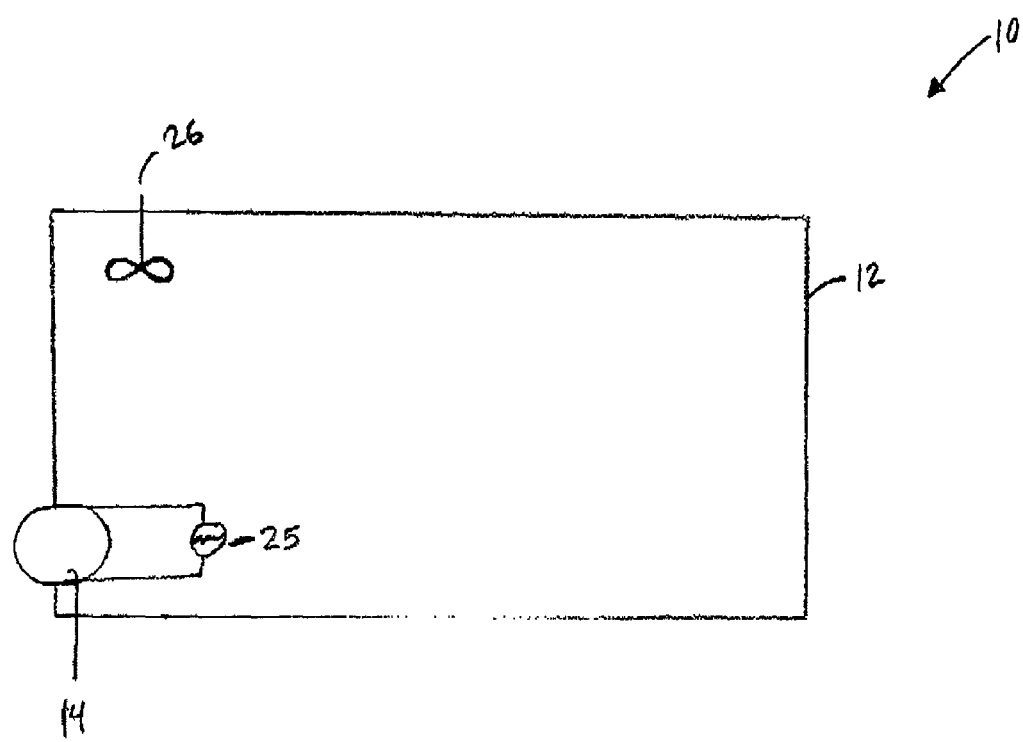
FIG. 8 of the drawings is a schematic representation of a sanitizing device in accordance with the present invention configured as a surrounding area sanitizing device.

As is shown in FIG. 8, sanitizing device 10 may be operatively configured as a surrounding area sanitizing device. In this embodiment sanitizing device 10 generally comprises housing 12, sanitizing component 14, and forced air means 26. For purposes of the present disclosure sanitizing component 14 may comprise an electrochemical, chemical, and/or corona cell, which may be powered by AC current and/or DC current 25 if necessary. In operation, a user places sanitizing device 10 in a surrounding environment, such as a room. Once positioned, sanitizing component 14 and forced air means 26 are activated by application of an applied potential. Forced air means 26 inputs the surrounding environment within housing 12, whereby the surrounding environment contacts sanitizing component 14 which purifies the surrounding environment. Once purified, the surrounding environment is expelled out of housing 12 through a porous portion of sanitizing component or an aperture associated therewith.

It will be understood that the term "sanitize" is herein defined as the function of sanitizing, disinfecting, and/or otherwise beneficially effecting surfaces, liquids, gasses, and/or surrounding environments.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A device for sanitizing a surface, the device comprising:
    a solid electrolyte conductor including an anode, a cathode, and a NaSICON electrolyte component;
    a housing operably connected to the solid electrolyte conductor wherein the housing is configured for placement of the solid electrolyte conductor adjacent the surface; and,
    a power source operably connected to the solid electrolyte conductor wherein at least one of the anode or the cathode are constructed from materials that upon operation of the solid electrolyte conductor, a sanitizing effect is imparted on the surface.

2. The device of claim 1, wherein ion conductivity across the NaSICON electrolyte component is greater than approximately $10^{-10}$ $(ohm\ cm)^{-1}$ at ambient temperatures.

3. A device for sanitizing a surface, the device comprising:
    a solid electrolyte conductor including an anode, a cathode, and an ion conducting electrolyte with ionic conductivity greater than approximately $10^{-10}$ $(ohm\ cm)^{-1}$ at ambient temperatures;
    a housing operably connected to the solid electrolyte conductor wherein the housing is configured for placement of the solid electrolyte conductor adjacent the surface; and,
    a power source operably connected to the solid electrolyte conductor wherein at least one of the anode or the cathode are constructed from materials that upon operation of the solid electrolyte conductor, a sanitizing effect is imparted on the surface.

* * * * *